(12) United States Patent
Brucker et al.

(10) Patent No.: US 9,714,919 B2
(45) Date of Patent: Jul. 25, 2017

(54) TRACE GAS CONCENTRATION IN ART MS TRAPS

(71) Applicant: MKS Instruments, Inc., Andover, MA (US)

(72) Inventors: Gerardo A. Brucker, Longmont, CO (US); Timothy C. Swinney, Fort Collins, CO (US); G. Jeffery Rathbone, Longmont, CO (US)

(73) Assignee: MKS Instruments, Inc., Andover, MA (US)

( * ) Notice: Subject to any disclaimer, the term of this patent is extended or adjusted under 35 U.S.C. 154(b) by 341 days.

(21) Appl. No.: 14/384,782

(22) PCT Filed: Mar. 13, 2013

(86) PCT No.: PCT/US2013/030801
§ 371 (c)(1),
(2) Date: Sep. 12, 2014

(87) PCT Pub. No.: WO2013/138446
PCT Pub. Date: Sep. 19, 2013

(65) Prior Publication Data
US 2015/0028882 A1    Jan. 29, 2015

Related U.S. Application Data

(60) Provisional application No. 61/610,092, filed on Mar. 13, 2012.

(51) Int. Cl.
*G01N 27/64* (2006.01)
*G01N 27/60* (2006.01)
(Continued)

(52) U.S. Cl.
CPC ............. *G01N 27/64* (2013.01); *G01N 1/405* (2013.01); *G01N 27/60* (2013.01); *H01J 49/06* (2013.01);
(Continued)

(58) Field of Classification Search
None
See application file for complete search history.

(56) References Cited

U.S. PATENT DOCUMENTS

| 4,743,167 A | 5/1988 | Martelli et al. |
| 4,785,666 A | 11/1988 | Bergquist |

(Continued)

FOREIGN PATENT DOCUMENTS

| CN | 1811408 A | 8/2006 |
| CN | 1926657 A | 3/2007 |

(Continued)

OTHER PUBLICATIONS

Hoffman, J. H., et al., "Phoenix Mars Mission—The Thermal Evolved Gas Analyzer," *J. Am. Soc. Mass. Spectrom.*, 19(10): 1377-1383 (2008).

(Continued)

*Primary Examiner* — Melissa Koval
*Assistant Examiner* — Felicia Farrow
(74) *Attorney, Agent, or Firm* — Hamilton, Brook, Smith & Reynolds, P.C.

(57) ABSTRACT

A method of detecting specific gas species in an ion trap, the specific gas species initially being a trace component of a first low concentration in the volume of gas, includes ionizing the gas including the specific gas species, thereby creating specific ion species. The method further includes producing an electrostatic potential in which the specific ion species are confined in the ion trap to trajectories. The method also includes exciting confined specific ion species (Continued)

with an AC excitation source having an excitation frequency, scanning the excitation frequency of the AC excitation source to eject the specific ion species from the ion trap, and detecting the ejected specific ion species. The method further includes increasing the concentration of the specific ion species within the ion trap relative to the first low concentration prior to scanning the excitation frequency that ejects the ions of the specific gas species.

15 Claims, 13 Drawing Sheets

(51) Int. Cl.
*H01J 49/06* (2006.01)
*H01J 49/42* (2006.01)
*G01N 1/40* (2006.01)
*H01J 49/16* (2006.01)

(52) U.S. Cl.
CPC ......... *H01J 49/4245* (2013.01); *H01J 49/162* (2013.01)

(56) References Cited

U.S. PATENT DOCUMENTS

| | | | |
|---|---|---|---|
| 5,142,143 A | 8/1992 | Fite et al. | |
| 5,426,300 A | 6/1995 | Voss et al. | |
| 6,326,615 B1 | 12/2001 | Syage et al. | |
| 6,545,268 B1 | 4/2003 | Verentchikov et al. | |
| 6,670,606 B2 | 12/2003 | Verentchikov et al. | |
| 7,034,292 B1 | 4/2006 | Whitehouse et al. | |
| 9,000,364 B2 | 4/2015 | Ermakov et al. | |
| 2002/0104962 A1 | 8/2002 | Danno et al. | |
| 2002/0162957 A1* | 11/2002 | Smith | G01M 3/202 250/292 |
| 2003/0141447 A1 | 7/2003 | Verentchikov et al. | |
| 2006/0289809 A1 | 12/2006 | Bonne et al. | |
| 2009/0294661 A1 | 12/2009 | Hashimoto et al. | |
| 2010/0084549 A1 | 4/2010 | Ermakov | |
| 2010/0163724 A1* | 7/2010 | Verbeck, IV | H01J 49/24 250/283 |
| 2011/0057095 A1 | 3/2011 | Loboda | |
| 2012/0014814 A1 | 1/2012 | Bonucci et al. | |

FOREIGN PATENT DOCUMENTS

| | | |
|---|---|---|
| CN | 101320016 A | 12/2008 |
| CN | 101385116 A | 3/2009 |
| CN | 101438375 A | 5/2009 |
| JP | 01-501570 A | 6/1989 |
| JP | 07-167050 A | 7/1995 |
| JP | 2002-181790 A | 6/2002 |
| JP | 2003-530675 A | 10/2003 |
| JP | 2009-289503 A | 12/2009 |
| JP | 2010-509732 A | 3/2010 |
| WO | WO 88/04774 A | 6/1988 |
| WO | WO 00/48229 | 8/2000 |
| WO | WO 01/78106 A2 | 10/2001 |
| WO | WO 2008/063497 A2 | 5/2008 |
| WO | WO 2010/129690 A2 | 11/2010 |

OTHER PUBLICATIONS

Ermakov, A., et al., "An Electrostatic Autoresonant Ion Trap Mass Spectrometer," *Rev. Sci. Instrum.*, 81: 13107-1-13107-8 (2010).
Ichimura, K., "Absorption and Desorption of Hydrogen, Deuterium, and Tritium for Zr—V—Fe Getter," *J. Vac. Sci. Technol. A*, 2(3): 1341-1347 (1984).
Manini, P., et al., "A Novel Approach in UHV Pumping of Accelerators: The Nextorr® Pump," *Proc. IPAC*, 1536-1538 (2011).
Peng, W.P., et al., "Laser-Induced Fluorescence/Ion Trap as a Detector for Mass Spectrometric Analysis of Nanoparticles," *Int. J Mass. Spectrom.*, 229: 67-76 (2003).
Notification Concerning Transmittal of International Preliminary Report on Patentability with International Preliminary Report on Patentability issued in International Application No. PCT/US2013/030801, "Trace Gas Concentration in ART MS Traps," mailed Sep. 25, 2014.
International Search Report and Written Opinion of the International Searching Authority from International Application No. PCT/US2013/030801, "Trace Gas Concentration in ART MS Traps," mailed May 21, 2013.
Japanese Application No. 2015-500553: Office Action with English language translation, dated Jun. 6, 2017.

\* cited by examiner

TRACE GAS CONCENTRATION IN ART MS TRAPS

RELATED APPLICATION(S)

This application is the U.S. National Stage of International Application No. PCT/US2013/030801, filed on Mar. 13, 2013, which designates the U.S., published in English, and claims the benefit of U.S. Provisional Application No. 61/610,092, filed on Mar. 13, 2012. The entire teachings of the above applications are incorporated herein by reference.

BACKGROUND OF THE INVENTION

A mass spectrometer is an analytical instrument that separates and detects ions according to their mass-to-charge ratio. Mass spectrometers can be differentiated based on whether trapping or storage of ions is required to enable mass separation and analysis. Non-trapping mass spectrometers do not trap or store ions, and ion densities do not accumulate or build up inside the device prior to mass separation and analysis. Examples in this class are quadrupole mass filters and magnetic sector mass spectrometers in which a high power dynamic electric field or a high power magnetic field, respectively, are used to selectively stabilize the trajectories of ion beams of a single mass-to-charge (m/q) ratio. Trapping spectrometers can be subdivided into two subcategories: dynamic traps, such as, for example, quadrupole ion traps (QIT) and static traps, such as the more recently developed electrostatic confinement traps.

Electrostatic confinement traps include the ion trap disclosed by Ermakov et al. in their PCT/US2007/023834 application and improved by Brucker et al. in their PCT/US2010/033750 application that confines ions of different mass-to-charge ratios and kinetic energies within an anharmonic potential well. The entire teachings of the aforementioned applications are incorporated herein by reference. The anharmonic resonant ion trap mass spectrometer (ART MS) is also provided with a small amplitude AC drive that excites confined ions. The amplitudes of oscillation of the confined ions are increased as their energies increase, due to a coupling between the AC drive frequency and the mass-dependent natural oscillation frequencies of the ions, until the oscillation amplitudes of the ions exceed the physical dimensions of the trap and the mass-selected ions are detected, or the ions fragment or undergo any other physical or chemical transformation.

SUMMARY OF THE INVENTION

Traps operated at pressures greater than about $1 \times 10^{-7}$ Torr can reach a maximum density of trapped ions due to, for example, space charge saturation resulting from electrostatic repulsion. The relative amounts of trapped ions of different atomic mass (AMU) closely reflect the composition of the sample gas mixture that was ionized, weighted by the relative ionization efficiency of the different ions. Consequently, trace gas components are ionized and trapped in the ion trap in proportion to their relative abundance, and given that the total number of trapped ions is limited, ion density of trace gas components can be lower than the detection limits of typical ion detectors.

Therefore, there is a need for improved methods of detection of trace gas components in an ion trap that minimize or eliminate the above mentioned problems.

There is provided a method of detecting specific gas species in an ion trap, the specific gas species initially being a trace component of a first low concentration in the volume of gas. The method includes ionizing the gas including the specific gas species, thereby creating specific ion species, and producing an electrostatic potential in which the specific ion species are confined in the ion trap to trajectories, at natural oscillation frequencies, in an electrode structure that includes first and second opposed mirror electrodes and a central lens electrode therebetween. The method further includes exciting confined specific ion species with an AC excitation source having an excitation frequency, scanning the excitation frequency of the AC excitation source to eject the specific ion species from the ion trap, and detecting the ejected specific ion species. The method also includes increasing the concentration of the specific ion species within the ion trap relative to the first low concentration prior to scanning the excitation frequency that ejects the ions of the specific gas species.

The method can further include increasing the concentration of specific gas species by selective removal of gas species other than the specific gas species. Selective removal can be by trapping and ejecting gas species other than the specific gas species prior to said scanning to eject the specific ion species, or alternatively, by selective sorption of the gas species other than the specific gas species with, for example, a non-evaporable getter, or by any other gas separation technique known in the art including cryogenic trapping, chemisorption and physisorption.

In yet another alternative, increasing the concentration of specific gas species can include selective sorption of the specific gas species with a non-evaporable getter, followed by desorption of the specific gas species from the non-evaporable getter. Ionizing the specific gas species can include selective photoionization of the specific gas species to increase the concentration of the specific ion species. The method can include data processing by integrating charge of specific gas species as a function of time. Photoionization can be by vacuum ultraviolet (VUV) photons with energies in the range of between about 8 eV and about 12 eV.

The method can further include, prior to said scanning of the excitation frequency to eject the specific ion species, concentrating the specific ion species by previously trapping and previously ejecting the specific ion species. In this case, the method can also include confining the previously ejected specific ion species in a second electrode structure, thereby preferentially accumulating the specific ion species in the second electrode structure, said scanning to eject the specific ion species further ejecting the previously ejected specific ion species. The method can further include filling the ion trap with a predetermined amount of gas.

An apparatus is also provided for detecting specific gas species in an ion trap, the specific gas species initially being a trace component of a first low concentration in a volume of gas. The apparatus includes an ionizer that ionizes the gas including the specific gas species, thereby creating specific ion species, and an electrode structure that produces an electrostatic potential in which the specific ion species are confined in the ion trap to trajectories, at natural oscillation frequencies, the electrode structure including first and second opposed mirror electrodes and a central lens electrode therebetween. The apparatus further includes an AC excitation source that excites confined specific ion species with an AC excitation frequency, a scan control that scans the excitation frequency of the AC excitation source to eject the specific ion species from the ion trap, and a detector that detects the ejected specific ion species. The apparatus is adapted to increase the concentration of the specific ion species within the ion trap relative to the first low concentration prior to the scan control scanning the excitation frequency that ejects the ions of the specific gas species.

The apparatus can include a non-evaporable getter that removes gas species other than the specific gas species by selective sorption of the gas species other than the specific gas species. Alternatively, if the specific gas species is hydrogen, the apparatus can further include a non-evaporable getter that increases the concentration of hydrogen by selective sorption followed by desorption of hydrogen from the non-evaporable getter.

The scan control can trap and eject other than the specific gas species prior to said scanning to eject the specific ion species. The ionizer can include a selective photoionization source that increases the concentration of the specific ion species. The photoionization source emits vacuum ultraviolet (VUV) photons with energies in the range of between about 8 eV and about 12 eV. The detector can integrate charge of specific gas species as a function of time.

The apparatus can further include a second electrode structure that confines previously ejected specific ion species and thereby concentrates previously trapped and previously ejected specific ion species, prior to the scan control scanning the excitation frequency to eject the specific ion species.

This invention has many advantages, such as increasing the concentration of specific ion species within the ion trap and thereby increasing the detection limits of trace gas components in a volume of gas.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
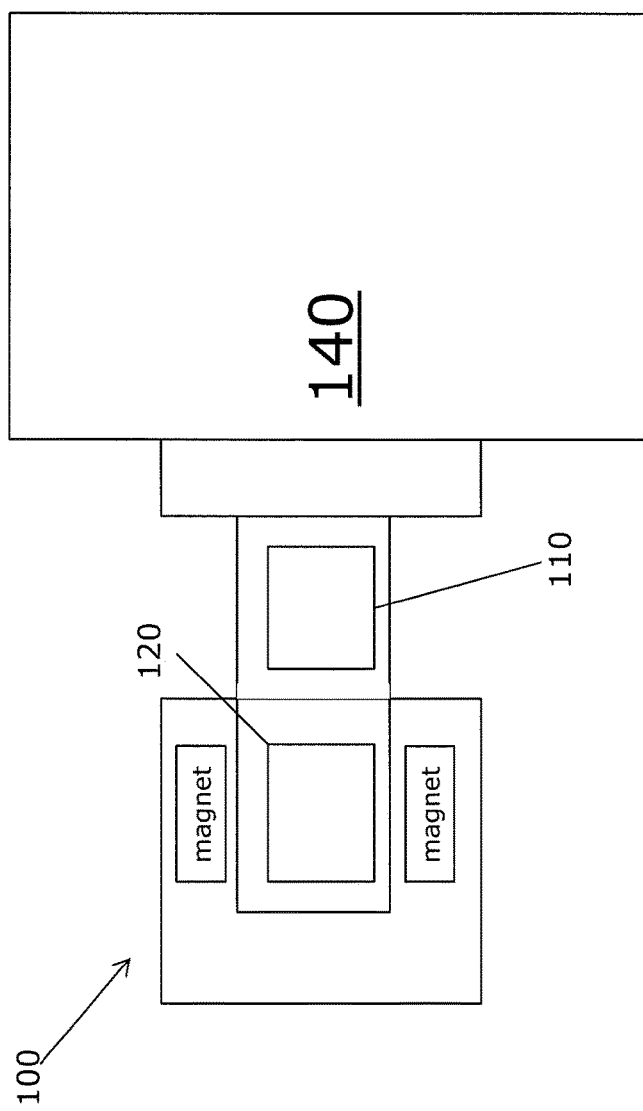
FIG. 1 is an illustration of a getter/ion pump connected to a vacuum chamber.

A description of example embodiments of the invention follows.

A method of detecting specific gas species in an ion trap, such as an ART MS, the specific gas species initially being a trace component of a first low concentration in the volume of gas, includes ionizing the gas including the specific gas species, thereby creating specific ion species. The method further includes producing an electrostatic potential in which the specific ion species are confined in the ion trap to trajectories, at natural oscillation frequencies, in an electrode structure that includes first and second opposed mirror electrodes and a central lens electrode therebetween. The method also includes exciting confined specific ion species with an AC excitation source having an excitation frequency, scanning the excitation frequency of the AC excitation source to eject the specific ion species from the ion trap, and detecting the ejected specific ion species. The method further includes increasing the concentration of the specific ion species within the ion trap relative to the first low concentration prior to scanning the excitation frequency that ejects the ions of the specific gas species.

The method can further include increasing the concentration of specific gas species by selective removal of gas species other than the specific gas species. Any gas separation technique known in the art can be used to concentrate the specific gas species. For example, gas separation techniques can include filtration, membrane separation, separation via one or more sorbents, cryogenic gas separation and trapping, ion trapping, and combinations thereof. In some embodiments, one or more sorbents are used to selectively remove one or more gas species. Suitable sorbents can include reactive sorbents, non-reactive sorbents, and combinations thereof. Sorbents can include, but are not limited to, molecular sieves, ion exchangers, getters (e.g., non-evaporable getters), and combinations thereof. In some embodiments, the method can include selective sorption of one or more unwanted gas species (i.e., the gas species other than the specific gas species). In other embodiments, the method can include selective sorption of the specific gas species, followed by desorption of the specific gas species.

In certain particular embodiments, the method can include selective sorption of the specific gas species with a non-evaporable getter, followed by the desorption of the specific gas species from the non-evaporable getter. The non-evaporable getter can be a part of a new generation of hybrid sorption/ion pumps based on non-evaporable getters (NEGs) as sorption elements, such as the NEXTorr® ion pumps. SAES Getters, Colorado Springs, Colo. Advantages of the combination of ART MS and hybrid sorption/ion pumps (hereinafter "getter/ion pumps") include the ability to:

1) develop low power, fast sampling systems capable of sampling atmospheric gases with low power requirements;

2) develop pulsed sampling systems wherein the sample gas is pulsed into the sampling volume;

3) develop a sampling system in which the gas-dependent pumping speed of the getter/ion pumps are used to specifically remove matrix (i.e., background) gases from a gas sample, thereby concentrating a specific gas species over time;

4) develop sampling systems in which only the ion pump or only the getter pump part of the getter/ion pump is active at a time thereby modifying the chemical composition of the gas being sampled over time;

5) develop sampling systems in which the operational conditions of the getter pump part of the getter/ion pump (e.g., temperature) are adjusted to tune its gas-dependent pumping speed; and 6) develop disposable pumping packages (i.e., consumables) that can be used in the field to capacity and then replaced with a new pumping package.

The getter/ion pump schematically illustrated in FIG. 1, such as the NEXTorr® ion pump 100, pumps gases by two different pumping mechanisms:

1) sorption by non-evaporable getter (NEG) 110: NEG pumps are compact, light weight, vibration-free devices able to deliver high pumping speeds with minimal power requirements. After an initial activation by heating to 500° C. for 1 hour, the getter 110 removes gases, other than inert gases (i.e., He, Ar, and other noble gases) at room temperature without electrical power. Hydrogen (and deuterium and tritium) is the only gas that is reversibly sorbed by a NEG pump, that is, it can be released back into the sampling system upon heating of the getter material. A sorption pump can be activated at the factory and then used in the field for substantial periods of time, provided that the vacuum is not compromised. The initial pumping speed and sorption capacity for various gases of a NEXTorr® pump are listed in Table 1.

TABLE 1

Initial pumping speed and sorption capacity for a NEXTorr ® pump

| Initial pumping speed (l/s) | Gas | NEG Activated | NEG Saturated |
|---|---|---|---|
| | $O_2$ | 100 | 3.5 |
| | $H_2$ | 100 | — |
| | CO | 70 | 6 |
| | $N_2$ | 40 | 5 |
| | $CH_4$ | 15 | 7 |
| | Ar | 6 | 6 |
| Sorption Capacity (Torr 1) | Gas | Single run capacity | Total Capacity |
| | $O_2$ | 5 | >500 |
| | $H_2$ | 135 | N/A |
| | CO | 0.6 | >120 |
| | $N_2$ | 0.3 | >25 |
| | $CH_4$ | 30 | 50,000 hrs at $10^{-6}$ Torr |

2) evacuation by an ion pump 120: the getter/ion pump also includes, behind the getter 110, an ion pump 120 that receives gas that flows via an optimized conduction path from the vacuum chamber 140 through the getter 110. The location of the ion pump 120 relative to the getter 110 in the NEXTorr® ion pump is designed to capture any gas or titanium particulates evolved from the ion pump 120 into the getter 110. The ion pump 120 in the NEXTorr® ion pump does not capture inert gases. Unlike the getter 110, the ion pump 120 can be turned off and on at any time, and therefore the pumping speed of the getter/ion pump 100 also depends on whether the ion pump 120 is on.

The getter/ion pump has a different pumping speed for different gases, enabling increasing the concentration of specific gas species relative to a first low concentration in a volume gas prior to analysis by selective sorption of the gas species other than the specific gas species using the getter/ion pump. For example, the high pumping speed of a getter/ion pump for $N_2$ and $O_2$ enables concentrating trace components of air, such as inert gases (e.g., Argon) from a static sample or a continuous slow inlet into the sampling system. Alternatively, increasing the concentration of specific gas species can include selective sorption of the specific gas species with the non-evaporable getter, followed by desorption of the specific gas species from the non-evaporable getter. For example, getter/ion pumps rapidly sorb hydrogen and its isotopes (i.e., deuterium, tritium) reversibly, and therefore the getter can be loaded with hydrogen and the other gas species can be removed with the ion pump or another vacuum pump, and then the getter can be heated to release the hydrogen, enabling isotopic analysis.

Figure 2:
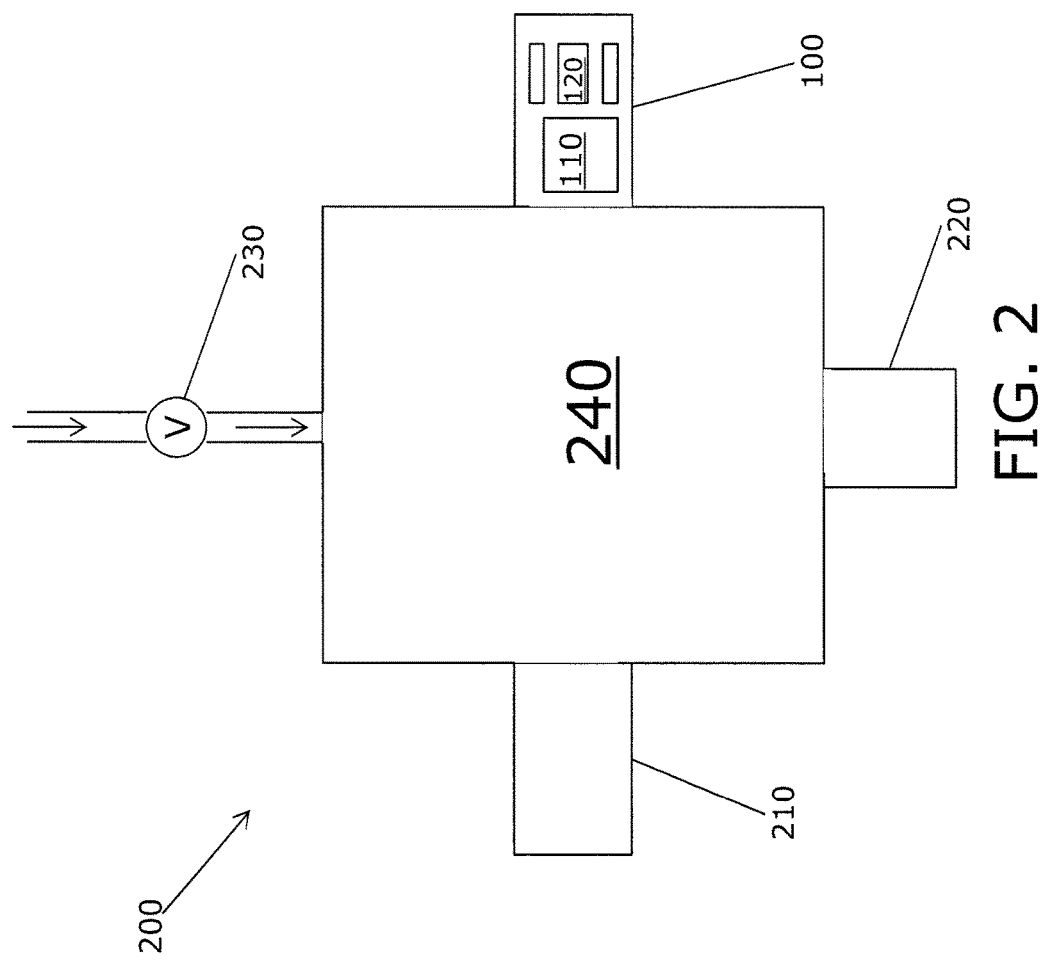
FIG. 2 is an illustration of a sampling system combining an ART MS device with a getter/ion pump according to this invention.

An example of a sampling system 200 combining ART MS device 210, getter/ion pump 100, and inlet 230 is shown in FIG. 2. The apparatus 200 can include a non-evaporable getter 110 that removes gas species other than the specific gas species by selective sorption of the gas species other than the specific gas species. Alternatively, as described above, if the specific gas species is hydrogen, the apparatus 200 can further include a non-evaporable getter 110 that increases the concentration of hydrogen by selective sorption followed by desorption of hydrogen from the non-evaporable getter 110. In other embodiments, this getter could be any other sorption device/material. In some embodiments, a sorption material could be attached to or coat the inside of the chamber. In some embodiments, a sorption material could be provided to the chamber in a removable cartridge form so that it can be swapped out once it is no longer capable of sorption.

The system 200 can be operated by continuous sampling or pulsed sampling. Under continuous sampling, the ART MS device 210 is pumped by the getter/ion pump 100 and gas is continuously allowed into the chamber 240 through an inlet 230, also called a leak, that can be, for example, a hole, a capillary, a frit, or a membrane, that regulates the pressure to a range suitable for the ART MS device 210. In this sampling system 200, the relative concentrations of gases in the initial sample are not preserved, as there is potential fractionation of the sample through the inlet 230 that continuously allows gas into the chamber 240, and different gases are pumped with different pumping speeds by the getter/ion pump 100, with some species potentially not pumped at all depending on whether the ion pump 120 is on in getter/ion pump 100. With the ion pump 120 off, sampling system 200 could be used to sample helium and argon in air, by continuously allowing air into the chamber 240, and allowing the concentration of helium and argon to increase. The relative amounts of $^3$He and $^4$He could then be measured by the ART MS device 210. After the measurement is completed, the chamber 140 can be evacuated by the auxiliary vacuum pump 220, clearing the chamber 240 for the next sample. The addition of a membrane to the inlet 230 enables, for example, sampling methane ($CH_4$) in water using polydimethylsulfoxide (PDMSO) membranes that have a high permeation rate of methane but also a significant permeation rate for water, taking advantage of the pumping speed the getter/ion pump 100 for methane being almost ten times slower than the corresponding pumping speed for water, thereby concentrating methane in chamber 240. Continuous sampling, however, limits the lifetime of getter/ion pumps 100 due to their limited storage capacity.

An alternative that addresses the storage capacity limitation of getter/ion pumps is pulsed sampling, wherein gas is introduced into the chamber 240 in controlled short pulses. The amount of gas introduced in each pulse is controlled for compatibility with the upper pressure limit of the ART MS device 210, by controlling the length of time of the pulse, the conductance of the pulsed inlet 230, or both. Suitable valves 230 include fast leak valves, such as solenoid valves (e.g., Parker), or piezoelectric valves (e.g., Key High Vacuum), or custom made fast sampling valves. See Rev. Sci. Instrum. 81 (201) p. 023106. Fast sampling valves are preferred because sampling times can be on the order of a few milliseconds. Once a pulse of gas is introduced into the chamber 240, there are at least three possible sampling scenarios: a) sample immediately if the pressure is low enough for the ART MS device 210, b) wait until the pressure is reduced by the getter/ion pump 100 to a pressure at which the ART MS device 210 can sample, and c) wait for the gas composition to change until the concentration of the specific gas species is increased to a level at which the ART MS device 210 can sample. Once sampling is completed, the getter/ion pump evacuates the chamber and provides a clean start for the next sample pulse. With pulsed sampling, gas is only introduced into the chamber 240 intermittently, so that the limited capacity of the getter pump 110 is only used when needed, extending the lifetime of the getter pump 110. It is also possible to load the chamber 240 with a fixed volume of gas, and then adjust the getter/ion gas-dependent pumping speeds to concentrate specific gas species. In addition, as shown in FIG. 2, it is also possible to combine a getter/ion pump 100 with another vacuum pump 220, such as a turbo molecular pump that can provide a final sample cleanup or gas independent pumping speed, and which can be isolated from the chamber 240 when it is not needed.

Figure 3A:
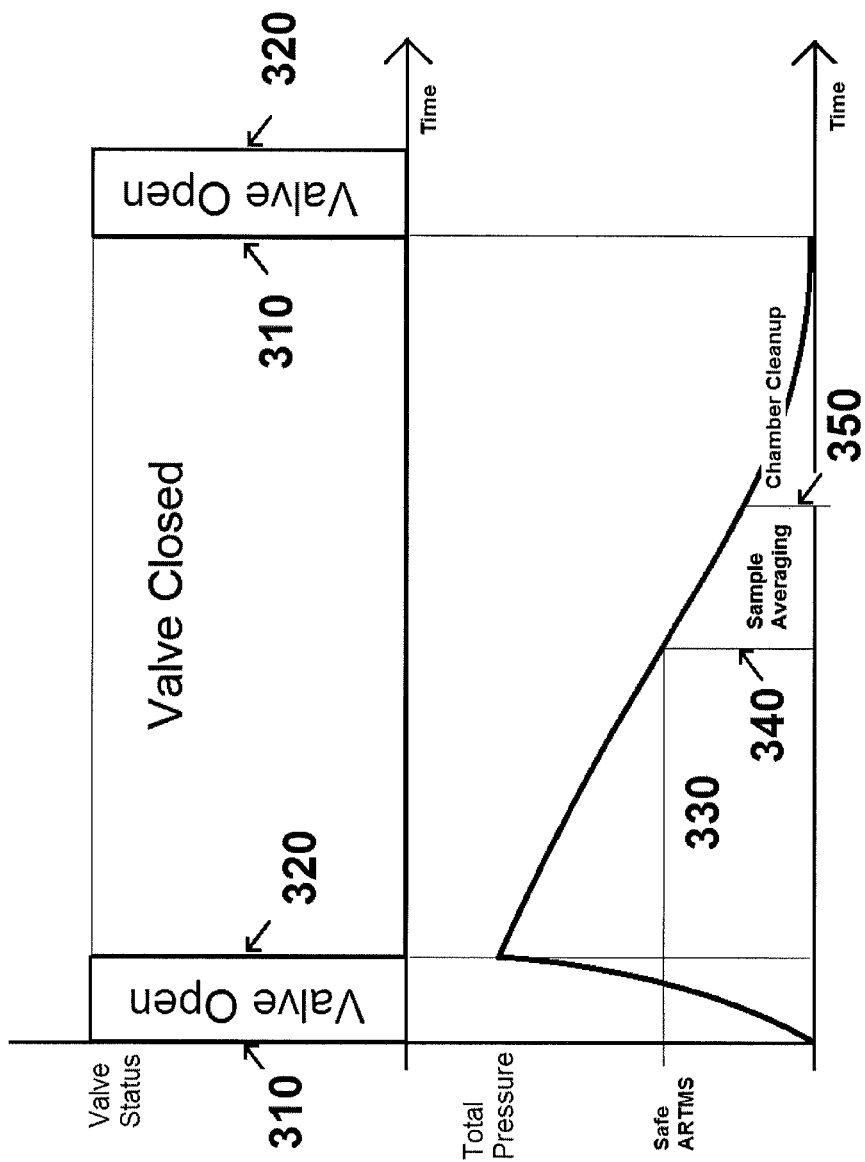
FIG. 3A is an illustration of a sequence of events and resulting gas pressure profile as a function of time in pulsed sampling using the system shown in FIG. 2 according to this invention.

FIG. 3A shows a possible sequence of events in pulsed sampling, using the apparatus illustrated in FIG. 2:

1) at step 310, valve 230 is opened and gas obtained directly from a sample environment or perfused through a membrane is briefly allowed into the otherwise sealed vacuum chamber 240 until the pressure reaches the maximum level compatible with the ART MS device 210;

2) at step 320, the valve 230 is then closed and the pressure is monitored at step 330 until it reaches suitable levels for the operation of the ART MS device 210 or until the concentration of specific gas species reaches levels at which the best ART MS data can be obtained;

3) at step 340, when ART MS spectral scans are averaged until the desired signal-to-noise ratio (SNR) is obtained; and 4) at step 350, the chamber 240 is then pumped out in preparation for another cycle.

Figure 3B:
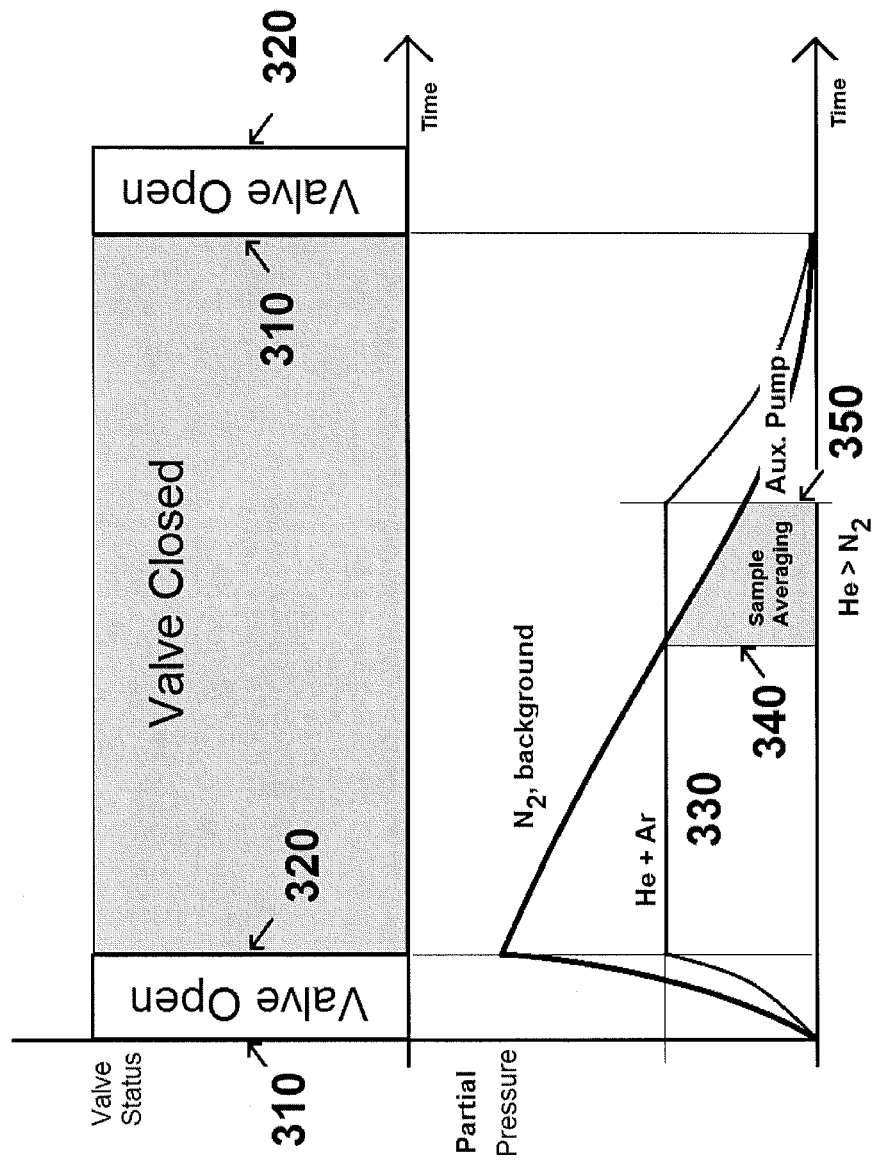
FIG. 3B is an illustration of a sampling cycle using the apparatus shown in FIGS. 1 and 2 and resulting gas pressure profile as a function of time in sampling nitrogen and helium from a sample of air according to this invention.

FIG. 3B shows an example sampling cycle using the apparatus shown in FIGS. 1 and 2 for sampling Argon and helium from a sample of air, where, given the gas-dependent pumping speeds of getter/ion pump 100, different gases will be evacuated at different times. The main components can be measured at the beginning of a cycle, and trace components that are pumped out slower (or not evacuated by the getter at all, such as helium) can be measured later in the sampling cycle. As shown in FIG. 3B, at step 310, valve 230 allows a pulse of air into the chamber 240, then, at step 320, valve 230 is closed, and the getter rapidly depletes the sample of active (i.e., background) components such as $N_2$, $O_2$, CO, $CO_2$, $H_2O$, etc., at step 330, while inert gases such as helium and Argon are left behind. If the concentration of inert gases is sufficiently high, then the ART MS device 210 obtains a gas spectrum at step 340. Otherwise, additional pulses of air can be introduced into the chamber 240 by repeating steps 310 and 320, further increasing the concentration of inert gases. After the gas spectrum is obtained during the sampling time 340, the auxiliary pump 220 is turned on at step 350, and the chamber 240 is cleared for a new sample.

A similar sampling cycle to the one shown in FIG. 3B can be used to detect volatile organic compounds (VOCs) in water by membrane introduction mass spectrometry (MIMS). Pumping speeds for VOCs using getter/ion pumps are lower than the pumping speeds for active components of air. VOCs pulsed into the chamber 240 after permeation through a membrane are present in small concentrations and along with a high concentration of water vapor, but the water is rapidly evacuated by the getter pump, enabling the ART MS to detect the VOCs.

Figure 4:
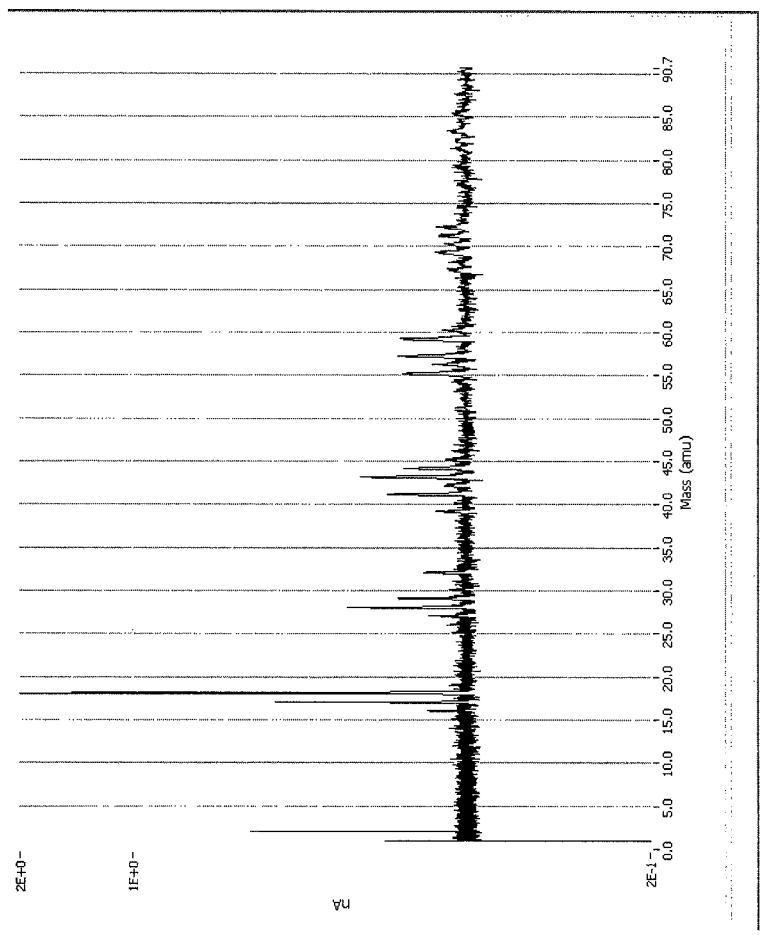
FIG. 4 is a typical mass spectrum resulting from vacuum (mechanical) pump oil contamination.

The above examples illustrate several methods of increasing the concentration of specific gas species prior to ionization and analysis by the ART MS device to improve the SNR of the ART MS. The SNR can also be improved by preferentially ionizing specific gas species, such as volatile organic compounds (VOCs), by vacuum ultraviolet (VUV) selective photoionization. VOCs can include chemical warfare agents, toxic industrial chemicals, and explosives, as well as hydrocarbons such as (mechanical) vacuum pump oils. An example mass spectrum resulting from pump oil contamination without peaks corresponding to background gases is shown in FIG. 4. Ionization of organic molecules with VUV photons with energies in a range of between about 8 eV and about 12 eV produces soft ionization, producing ions without significant fragmentation of the organic molecules. Photoionization causes the organic molecule to lose an electron through single photon ionization (SPI), in which energy is coupled from the photon directly into the electronic states of the molecule. Air components (i.e., $N_2$, $O_2$, Ar, etc.) are not ionized by VUV photons. The light for photoionization can be produced by, for example, VUV lamps such as He, Ar, Kr, Xe, and $D_2$ lamps obtained from lamp manufacturers such as Hamamatsu, Heraeus, Cathodeon, and Optimare. Choosing different lamp fill gases can also tailor the energy of the ionization process and provide additional selectivity for ionization. Other light sources include extreme ultraviolet (EUV) laser sources, and frequency doubled or tripled pulsed lasers.

Figure 5:
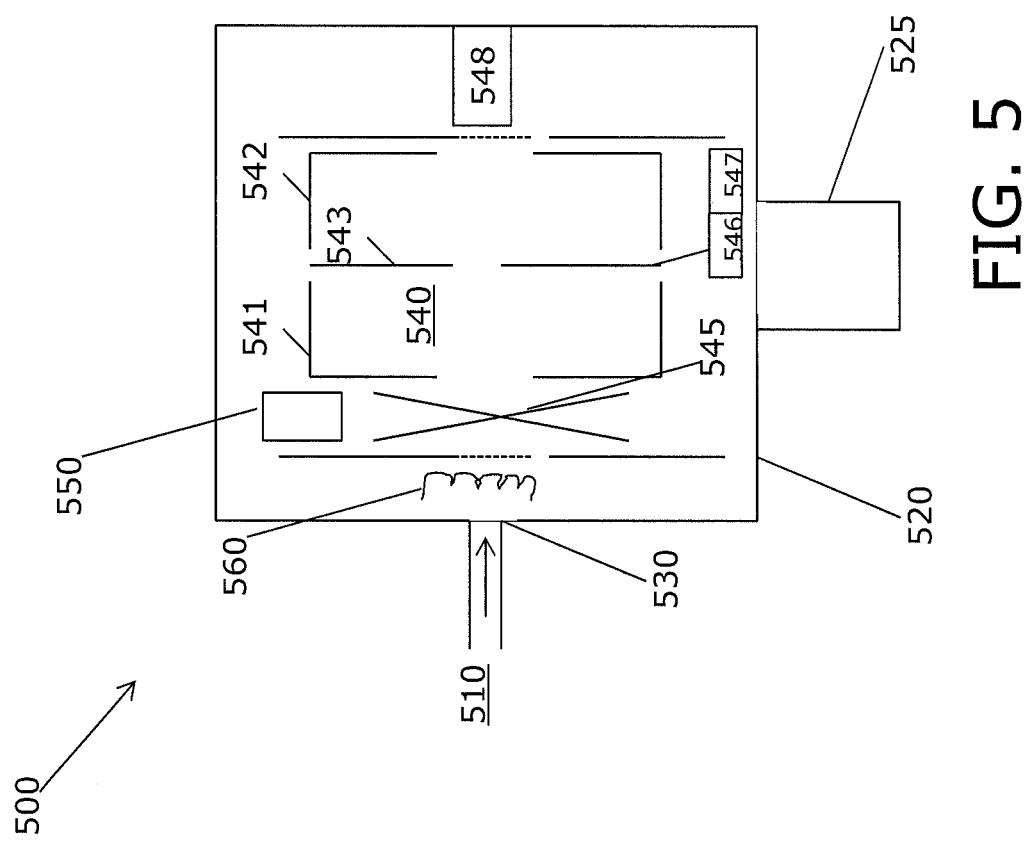
FIG. 5 is an illustration of an apparatus for detection of organic compounds according to this invention.

An apparatus 500 for detection of specific gas species, such as organic compounds, with an ART MS is shown in FIG. 5. The apparatus 500 includes an ionizer (550; 560) that ionizes the gas including the specific gas species, thereby creating specific ion species, and an electrode structure (541; 542; 543) that produces an electrostatic potential in which the specific ion species are confined in the ion trap to trajectories, at natural oscillation frequencies, the electrode including a first 541 and a second 542 opposed mirror electrodes and a central lens electrode 543 therebetween. The apparatus further includes an AC excitation source 546 that excites confined specific ion species with an AC excitation frequency, a scan control 547 that scans the excitation frequency of the AC excitation source 546 to eject the specific ion species from the ion trap 540, and a detector 548 that detects the ejected specific ion species. An atmospheric sample 510 containing specific gas species is introduced into a high vacuum system 520 through a differential pressure inlet 530. FIG. 5 illustrates a single stage differential pressure inlet, that is, an inlet that establishes a pressure differential between the sample 510 and the ion trap 540, while FIG. 8 below illustrates a two stage differential pressure inlet. The low pressure gas diffuses into the ion trap 540 and a VUV source 550 ionizes the specific gas species directly in the ionization region of the trap 545. The ion trap 540 can include an ionizer including photoionization (PI) source 550 as well as electron impact ionization (EII) using filament 560, which can be used in parallel or sequentially with PI. EII ionizes both air components and organic compounds, so that the trap 540 fills with mostly air gas ions, and the organic compound ions are diluted by the air component ions. EII can used sequentially with PI to check that a sufficient sample has been introduced into the trap 540. When ionization is switched to photoionization, only organic compounds are ionized and stored in the trap 540, concentrating the organic compound ions (i.e., specific ion species), and providing enhanced detection limits for VOCs relative to EII. A lens can be used with the VUV source 550 to focus the light into a well defined ionization region 545 to maximize the number of specific ion species trapped in ion trap 540. The VUV source 550 can include multiple lamps for increased ionization selectivity, and can be oriented orthogonally to the cylindrical axis of the ART MS trap 540 as shown in FIG. 5, or coaxial with ART MS trap 540 as described below.

Figure 6:
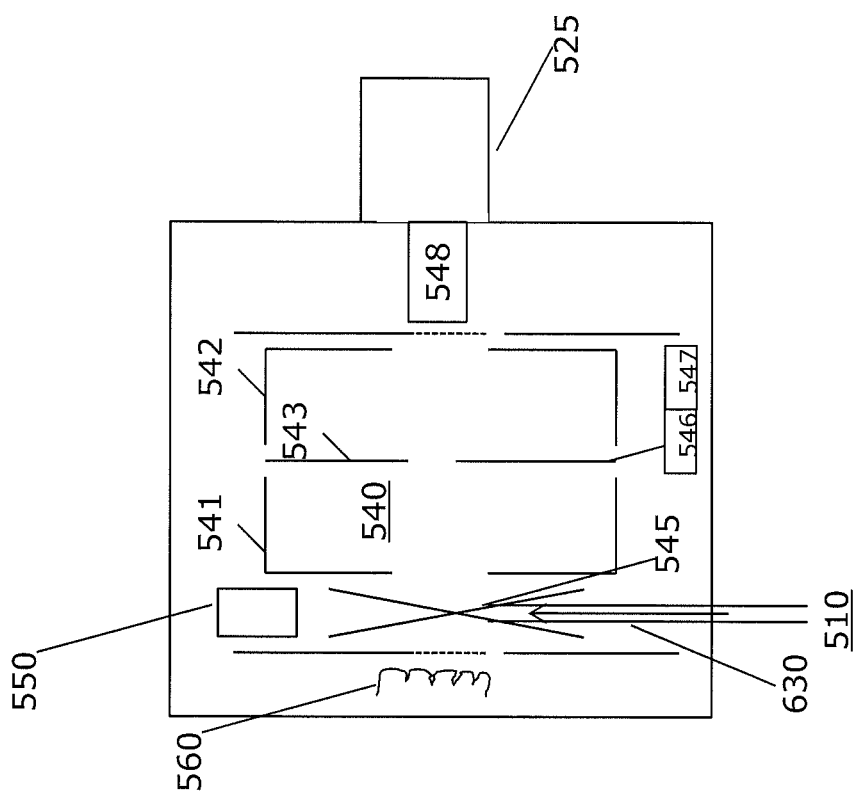
FIG. 6 is an illustration of an apparatus for detection of organic compounds including a capillary tube for introducing gas into the apparatus according to this invention.
Figure 7:
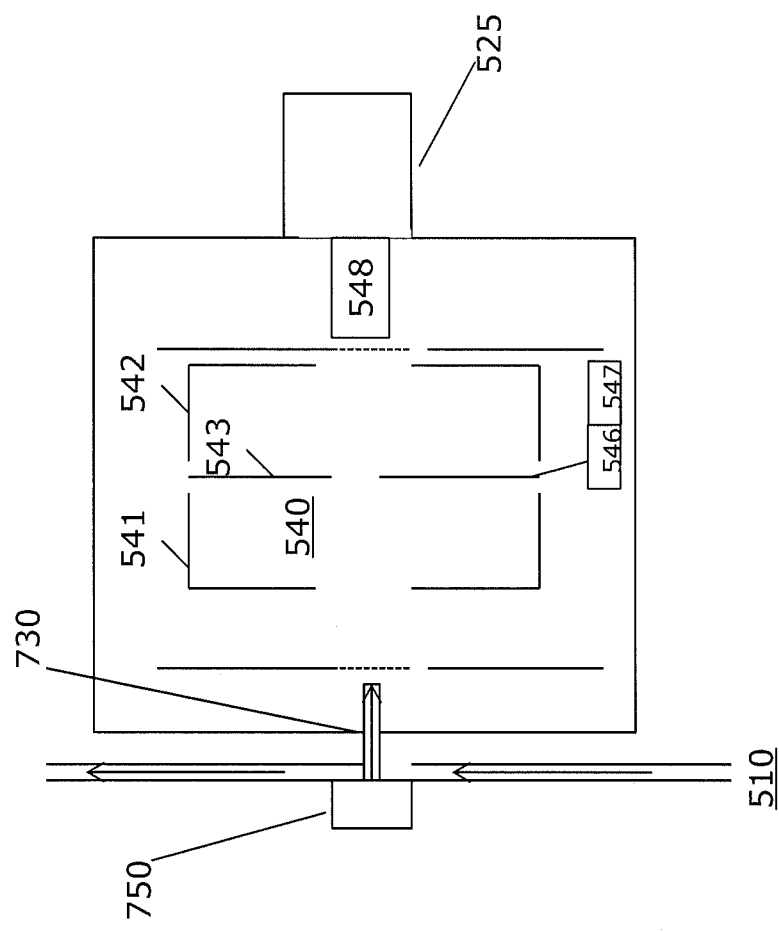
FIG. 7 is an illustration of an apparatus for detection of organic compounds including a capillary tube oriented coaxially with the cylindrical axis of the ART MS trap for introducing gas into the apparatus according to this invention.

An alternative gas inlet design, shown in FIG. 6, includes a capillary tube 630 that introduces gas into the focusing region 545 of the VUV source 550. The capillary tube 630 can be oriented orthogonal to the cylindrical axis of the ART MS trap 540, as shown in FIG. 6, or coaxial with the ART MS trap 540, as shown in FIG. 7 where coaxial capillary tube 730 is shown coaxial with the cylindrical axis of the ART MS trap, the capillary tube 730 introducing the sample gas 510 orthogonally to the cylindrical axis of the ART MS trap. The VUV source 550 is also shown coaxial with the ART MS trap 540 in FIG. 7. The capillary tube 730 can also be a pinhole or a skimmer.

Figure 8:
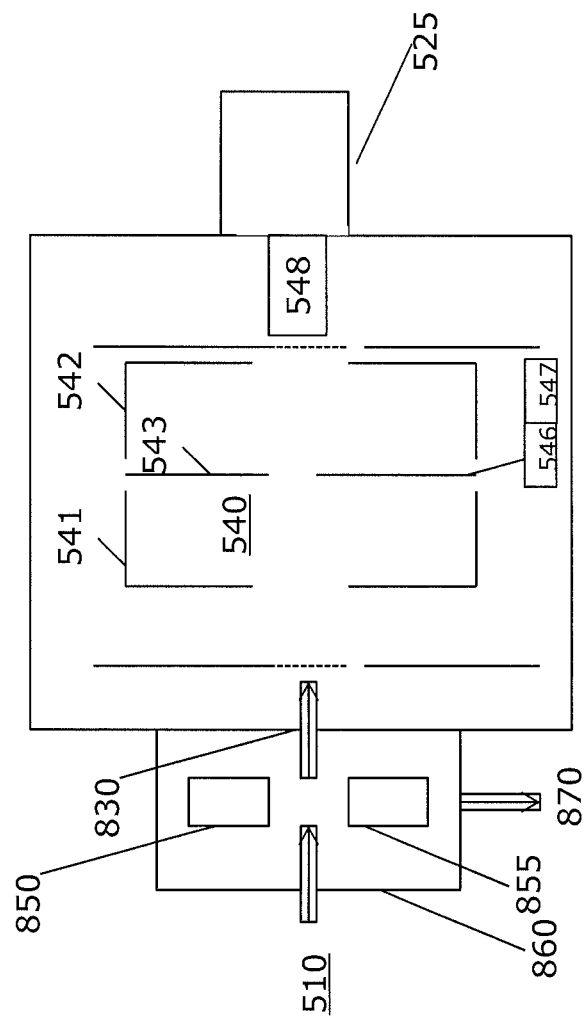
FIG. 8 is an illustration of an apparatus for detection of organic compounds including dual VUV lamp sources in a two stage differentially pumped system according to this invention.

An alternative VUV source design, shown in FIG. 8, includes two VUV sources 850 and 855 in a two stage differentially pumped sampling system that can be used to sample air at atmospheric pressure. Air containing the specific gas species is introduced into a chamber 860 having an intermediate pressure maintained by pump 870 that can be from a few Torr to mTorr levels. The gas is ionized by VUV light from lamps 850 and 855, and the formed ions are transferred into the ART MS trap 540 through a capillary 830 or a skimmer.

Figure 9:
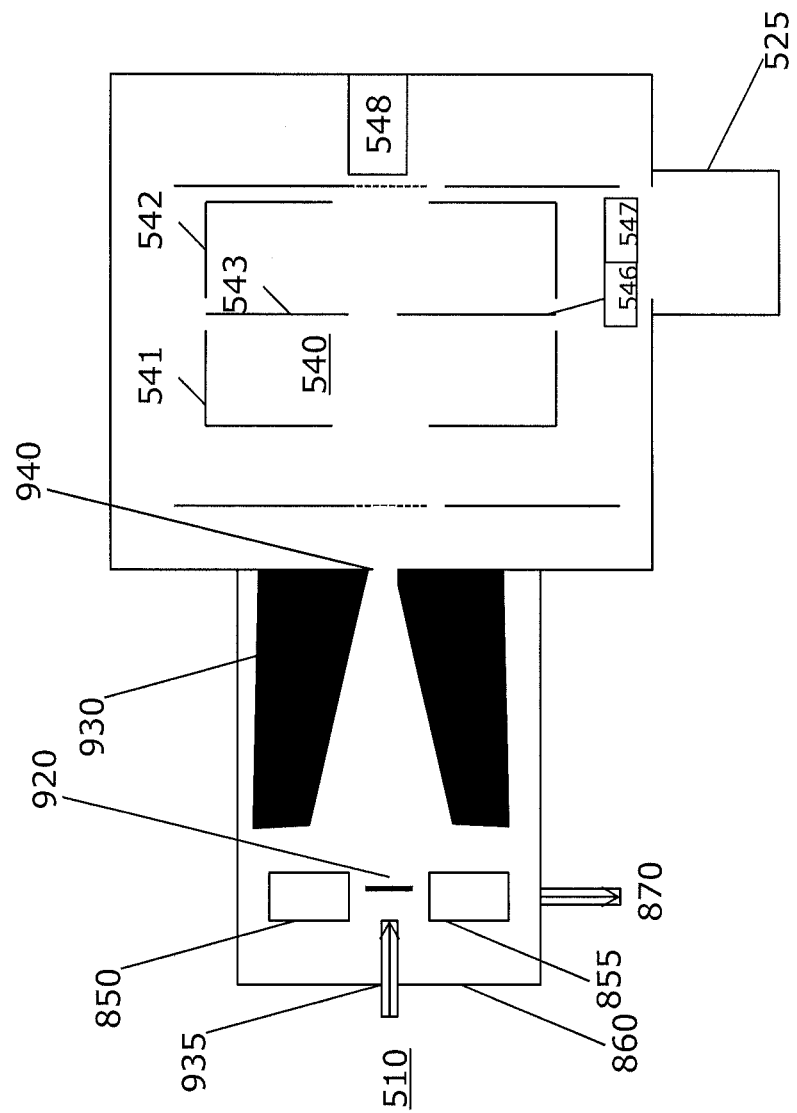
FIG. 9 is an illustration of an apparatus for detection of organic compounds including an ion funnel according to this invention.

The reduced pressure inside chamber 860 reduces buildup of contamination, enables the use of ion lenses or an ion funnel 930, as shown in FIG. 9, and enhances flexibility in the placement of the VUV lamps 850 and 855 (which can be different lamps for enhanced selectivity). Chamber 860 can also include a corona discharge to create ions inside chamber 860 from specific gas species that are not efficiently ionized by SPI. In the design shown in FIG. 9, an air sample is differentially pumped into an intermediate chamber 860 (using a vacuum pump 870 such as a diaphragm pump or the inter-stage of a turbo pump) at a pressure in a range of between about 1 Torr and about 30 Torr. The gas that effuses from the capillary 935 is ionized by the VUV lamps 850 and 855, and the ions are coupled into the ART MS trap 540 by the ion funnel 930. A beam stop 920 prevents neutrals effusing from the capillary 935 from directly reaching the aperture 940 of the ion funnel 930, but allows ions to go around the beam stop 920 and be focused into the aperture 940 for transfer into the ART MS trap 540.

For detection of total organic compounds (TOC), data processing of mass spectra obtained using the designs shown in FIGS. 5-9 described above includes integrating over time the charge ejected from the trap for peaks at masses greater than 45 amu (see mass spectrum shown in FIG. 4). The percent TOC (TOC %) is the ratio of TOC charge over the total charge, obtained by integrating over time the charge for the entire spectrum. The absolute TOC partial pressure is the TOC % multiplied by the total pressure measured using, for example, an ionization gauge.

Figure 12:
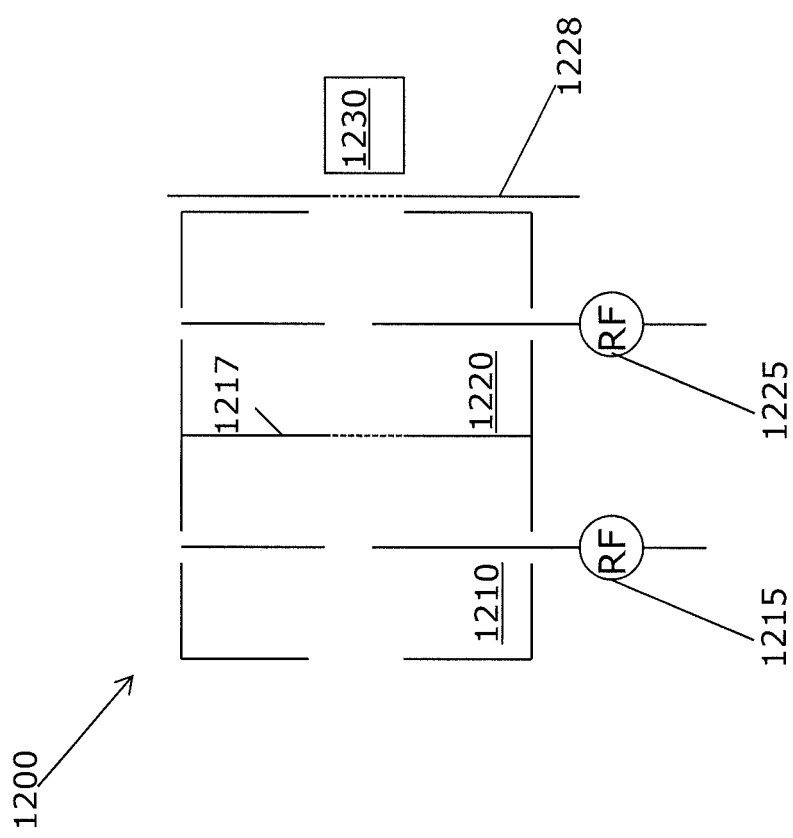
FIG. 12 is an illustration of a tandem trap ART MS device according to this invention.

Yet another way to improve the SNR of an ART MS device is by trapping and ejecting other than the specific gas species using scan control 547 and AC excitation source 546, shown in FIG. 5, prior to said scanning to eject the specific ion species, or, alternatively, prior to said scanning of the excitation frequency to eject the specific ion species, concentrating the specific ion species by previously trapping and previously ejecting the specific ion species, and, optionally, confining the previously ejected specific ion species in a second electrode structure 1220, shown in FIG. 12, thereby preferentially accumulating the specific ion species in the second electrode structure, said scanning to eject the specific ion species further ejecting the previously ejected specific ion species. In this apparatus all ions are first accumulated in the first trap 1210, and only the specific ion species are transferred to the second trap 1220 using an AC excitation scan focused on the natural oscillation frequency of the specific ions. The specific ions excited in the first trap 1210 reach the grid structure on grid plate 1217 and cross over to the right side due to their increased amplitude and energy. Increasing amounts of specific ions are accumulated in the second trap 1220, as the AC excitation is repeatedly scanned in the first trap 1210. Variations in this methodology include the possibility of simultaneously accumulating two independent specific ion species in the trap with accumulation times that are proportional to their relative concentrations, i.e. longer accumulation times for the lowest concentration specific ion species and shorter accumulation times for the higher concentration specific ion species. Under this mode of operation, the specific ion species of higher concentration are ejected more often than the lower concentrations species that require longer integration times to reach above detection limits. A more elaborate instrumental setup could also involve a tandem structure as shown in FIG. 12 in which a single trap is used to accumulate specific ion species, which are then selectively ejected into multiple second parallel traps using focusing lenses and deflectors to direct the ions. In this approach, the independent specific ion species are accumulated in dedicated second traps that are subsequently scanned when the ion concentrations reach levels above their detection limits. An alternative way to more rapidly accumulate ions in a second trap as shown in FIG. 12 could involve the use of multiple parallel first traps to accumulate the same specific ion species and to feed only those ions into a single second trap to increase the rate of ion accumulation and to accelerate filling times in the second trap. Furthermore, more than two traps could be used in tandem (serially), where the subsequent traps are used to store specific ions using AC excitation to displace ions from one trap to the next one. Once the traps are filled with ions, AC excitation is used to move the ions one-by-one into the detector.

Figure 10:
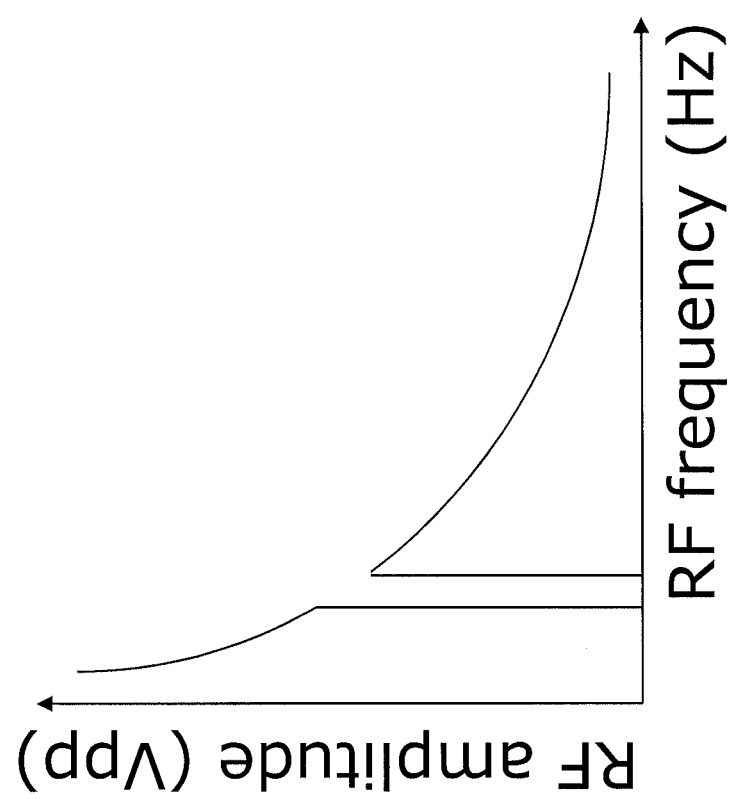
FIG. 10 is a graph of RF amplitude as a function of frequency for an example RF excitation frequency scan containing one RF notch according to this invention.

One approach to concentrating specific ion species of a trace gas of interest inside an ART MS device with continuous ion filling is by scanning the RF excitation frequency rapidly and with at least one RF notch, that is, a zero or near zero RF amplitude, as shown in FIG. 10, at at least one frequency corresponding to the ejection frequency of at least one trace gas of interest. The RF amplitude aside from the notch can be higher than the standard amplitude, so that ions other than the trace gas of interest are efficiently ejected out of the ART MS even at a high frequency sweep rate. The sweep rate is increased so that the ion populations are not readily replenished between scans and the electron emission current is also reduced so that the rate of ion formation is reduced between scans. If this scanning process is repeated several times, the concentration of ions of the trace gas of interest (i.e., the only ions that are not ejected from the trap) will increase relative to the concentration of all other ions. After several cycles of notched RF excitation scans, a final RF excitation scan centered at the ejection frequency of the trace gas ions will improve the SNR of the ART MS device for the trace gas of interest.

Figure 11:
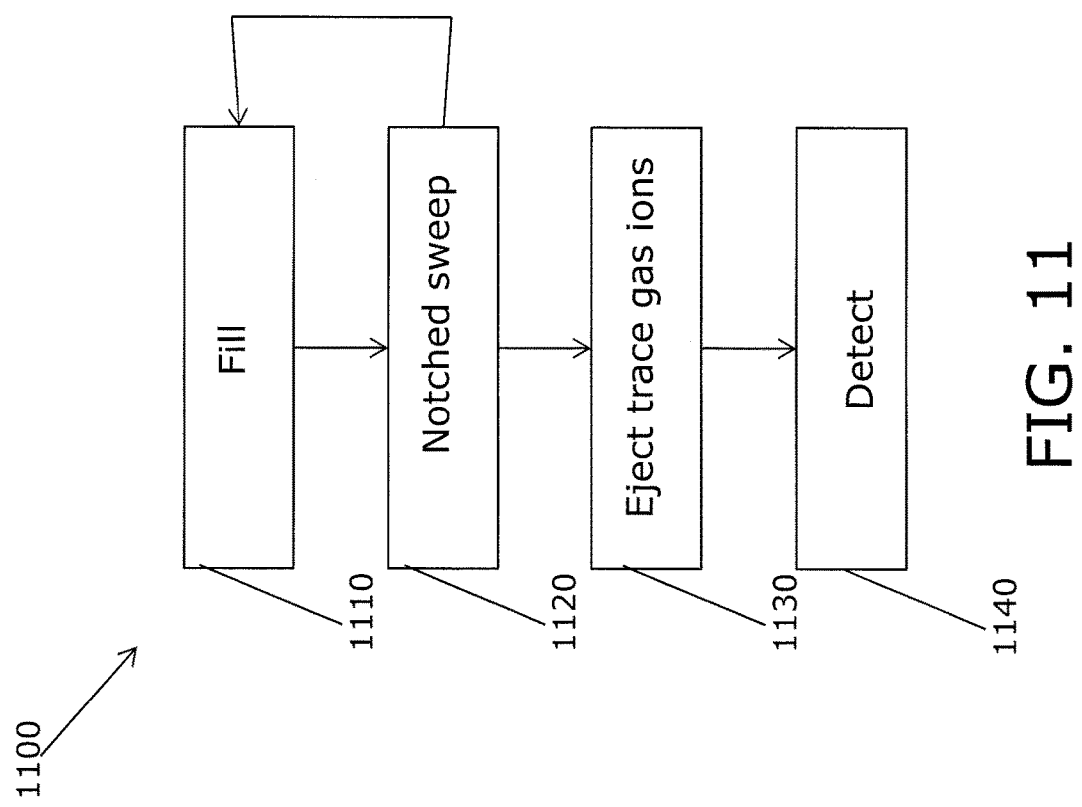
FIG. 11 is a flowchart of a combination of pulsed filling and notched concentration sweeps according to this invention.

An alternative to the above RF excitation scanning method is to combine it with pulsed filling of the trap. In this method illustrated in flowchart 1100, shown in FIG. 11, the trap is filled with ions at step 1110 for a predetermined amount of time and then a notched concentration sweep is performed at step 1120 to eject ions other than the trace gas ions of interest. Note that the trace gas ions of interest can consist of more than one mass. The process of pulsed filling followed by a notched concentration sweep can be repeated several times. Pulsed filling enables control over the number of ions introduced into the trap with each pulse, thereby avoiding charge saturation between scans. After several cycles of pulsed filling and notched concentration scans, the concentration of trace gas ions of interest relative to other species should increase. The RF amplitude of the notched concentration scans can be increased for improved ejection efficiency. At the end of this concentration step, without introducing any more ions into the trap, a final AC excitation frequency sweep at step 1130 ejects the trace gas ions of interest from the trap, followed by detection at step 1140.

The parameters that can be adjusted for the pulsed filling method include: 1) the fill time and electron emission current that control the number of ions introduced into the trap with each cycle, 2) the scan time and RF amplitude for the notched concentration sweep, 3) the number of notched concentration sweeps, each one preceded by a controlled ion filling, and 4) the RF amplitude, sweep time, and frequency range of the trace gas ejection sweep.

The trace gas ejection sweep can be used to send the trace gas ions of interest into a second trap, as shown in FIG. 12. Tandem trap ART MS device 1200 includes a first trap 1210 and a second trap 1220 connected in series. Each of the first trap 1210 and second trap 1220 can independently store ions, and each trap has a first RF source 1215 and a second RF source 1225 that can eject ions. The device 1200 can be used to select individual ion masses to be transferred from the first trap 1210 (general storage trap) to the second trap 1220 (selective storage trap) using narrow frequency sweeps centered around the ejection frequency of the trace gas ions of interest. After a few cycles of selective transfer of trace gas ions of interest, which can include multiple ion masses, from first trap 1210 into second trap 1220, a final frequency sweep can be applied with the second RF source 1225 to eject and detect the accumulated trace gas ions of interest using detector 1230. The tandem trap device 1200 can be used with continuous or pulsed filling. The transfer of ions from the first trap 1210 to the second trap 1220 occurs simply because the excitation frequency scan provided by the RF source 1215 excites the energy of the specific ions and brings them close to the grid in plate 1217 making it possible to transmit and store ions in the second trap 1220. A time variant implementation of the voltage on plate 1217 could lower the grid voltage when ions need to be transmitted into the second trap 1220 and raised again once ions are transmitted and stored, making grid plate 1217 operate as an electronic ion valve. The voltage on the exit plate 1228 leading to the detector 1230 could also be changed prior to ejection of the ions from the second trap 1220 to ensure that all stored ions exit towards the detector 1230 and are not lost to plate 1217 or sent back into the first trap 1210.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of detecting specific gas species in an ion trap, the specific gas species initially being a trace component of a first low concentration in a volume of gas, the method comprising:
   i) ionizing the gas including the specific gas species, thereby creating specific ion species;
   ii) producing an electrostatic potential in which the specific ion species are confined in the ion trap to trajectories, at natural oscillation frequencies, in an electrode structure that includes first and second opposed mirror electrodes and a central lens electrode therebetween;
   iii) exciting confined specific ion species with an AC excitation source having an excitation frequency;
   iv) scanning the excitation frequency of the AC excitation source to eject the specific ion species from the ion trap; and
   v) detecting the ejected specific ion species,
   the method further comprising increasing the concentration of the specific ion species within the ion trap relative to the first low concentration prior to scanning the excitation frequency that ejects the ions of the specific gas species;
   the method further comprising increasing the concentration of the specific gas species by either:
   a) selective removal of gas species other than the specific gas species by selective sorption of the gas species other than the specific gas species with a non-evaporable getter; or
   b) selective sorption of the specific gas species with a non-evaporable getter, followed by desorption of the specific gas species from the non-evaporable getter.

2. The method of claim 1, wherein ionizing the specific gas species includes selective photoionization of the specific gas species to increase the concentration of the specific ion species.

3. The method of claim 2, further including data processing by integrating charge of specific gas species as a function of time.

4. The method of claim 2, wherein photoionization is by vacuum ultraviolet (VUV) photons with energies in the range of between about 8 eV and about 12 eV.

5. The method of claim 1, further comprising, prior to said scanning of the excitation frequency to eject the specific ion species, concentrating the specific ion species by previously trapping and previously ejecting the specific ion species.

6. The method of claim 5, wherein the electrode structure is a first electrode structure, and further including confining the previously ejected specific ion species in a second electrode structure, thereby accumulating the specific ion species in the second electrode structure, said scanning to eject the specific ion species further ejecting the previously ejected specific ion species.

7. The method of claim 1, further including filling the ion trap with a predetermined amount of gas.

8. An apparatus for detecting specific gas species in an ion trap, the specific gas species initially being a trace component of a first low concentration in a volume of gas, the apparatus comprising:
   i) an ionizer that ionizes the gas including the specific gas species, thereby creating specific ion species;
   ii) an electrode structure that produces an electrostatic potential in which the specific ion species are confined in the ion trap to trajectories, at natural oscillation frequencies, the electrode structure including first and second opposed mirror electrodes and a central lens electrode therebetween;
   iii) an AC excitation source that excites confined specific ion species with an AC excitation frequency;
   iv) a scan control that scans the excitation frequency of the AC excitation source to eject the specific ion species from the ion trap; and
   v) a detector that detects the ejected specific ion species, the apparatus adapted to increase the concentration of the specific ion species within the ion trap relative to the first low concentration prior to the scan control scanning the excitation frequency that ejects the ions of the specific gas species,
   the apparatus further comprising a non-evaporable getter that either:
      a) removes gas species other than the specific gas species by selective sorption of the gas species other than the specific gas species; or
      b) increases the concentration of the specific gas species by selective sorption followed by desorption of the specific gas species from the non-evaporable getter.

9. The apparatus of claim 8, wherein the specific gas species is hydrogen and the non-evaporable getter increases concentration of hydrogen by selective sorption followed by desorption of hydrogen from the non-evaporable getter.

10. The apparatus of claim 8, wherein the scan control traps and ejects other than the specific gas species prior to said scanning to eject the specific ion species.

11. The apparatus of claim 8, wherein the ionizer includes a selective photoionization source that increases the concentration of the specific ion species.

12. The apparatus of claim 11, wherein the photoionization source emits vacuum ultraviolet (VUV) photons with energies in the range of between about 8 eV and about 12 eV.

13. The apparatus of claim 11, wherein the detector integrates charge of specific gas species as a function of time.

14. The apparatus of claim 8, further comprising a second electrode structure that confines previously ejected specific ion species and thereby concentrates previously trapped and previously ejected specific ion species, prior to the scan control scanning the excitation frequency to eject the specific ion species.

15. The method of claim 1, wherein the specific gas species is hydrogen and the non-evaporable getter increases the concentration of hydrogen by selective sorption followed by desorption of hydrogen from the non-evaporable getter.

* * * * *